United States Patent [19]

Bombardelli

[11] Patent Number: 5,484,833

[45] Date of Patent: Jan. 16, 1996

[54] DERIVATIVES OF NON-STEROIDAL ANTI-INFLAMMATORY, ANALGESIC AND/OR ANTIPYRETIC SUBSTANCES, THEIR USE AND PHARMACEUTICAL FORMULATIONS CONTAINING THEM

[75] Inventor: Ezio Bombardelli, Milan, Italy

[73] Assignee: Indena S.p.A., Italy

[21] Appl. No.: 922,636

[22] Filed: Jul. 30, 1992

[30] Foreign Application Priority Data

Jun. 11, 1992 [GB] United Kingdom ............... 9212450

[51] Int. Cl.$^6$ ..................................... A61K 9/70
[52] U.S. Cl. ............................ 424/449; 514/121
[58] Field of Search ....................... 424/449, 450, 424/514

[56] References Cited

U.S. PATENT DOCUMENTS

| | | | |
|---|---|---|---|
| 4,738,848 | 4/1988 | Yoshida et al. | 424/448 |
| 5,154,930 | 10/1992 | Popescu et al. | 429/489 |
| 5,204,112 | 4/1993 | Hope et al. | 424/450 |

Primary Examiner—Thurman K. Page
Assistant Examiner—Neil Levy
Attorney, Agent, or Firm—Kirschstein et al.

[57] ABSTRACT

Novel derivatives of non-steroidal anti-inflammatory, analgesic and/or antipyretic substances are provided which are useful in the treatment of superficial or deep inflammatory conditions, such as erythemas of various origins, inflammation of the joints or inflammation of bacterial origin.

The derivatives of the invention are salts of non-steroidal anti-inflammatory, analgesic and/or antipyretic substances (NSAs) and phosphatidic acids and preferably have the formula $$[NSA]_x[PA]_y$$

wherein

NSA represents a cation derived from said non-steroidal anti-inflammatory analgesic and/or antipyretic substance, PA represents a phosphatidic acid or a mixture of different phosphatidic acids, and x:y is from 2:1 to 1:2.

11 Claims, No Drawings

DERIVATIVES OF NON-STEROIDAL ANTI-INFLAMMATORY, ANALGESIC AND/OR ANTIPYRETIC SUBSTANCES, THEIR USE AND PHARMACEUTICAL FORMULATIONS CONTAINING THEM

BACKGROUND OF THE INVENTION

The present invention relates to new derivatives of non-steroidal anti-inflammatory, analgesic and/or antipyretic substances, to processes for their production and to novel pharmaceutical compositions and dosage forms containing them.

More specifically, the present invention relates to the therapeutic use of new salts of non-steroidal anti-inflammatory analgesic and/or antipyretic substances that are useful in the treatment of superficial or deep inflammatory conditions, such as erythemas of various origins, inflammation of the joints or inflammation of bacterial origin. In the present specification, the abbreviation "NSA" will be used to denote the expression "non-steroidal anti-inflammatory, analgesic and/or antipyretic substance".

Typical NSAs in widespread use include acetylsalicylic acid (aspirin), 4-(2-methylpropyl)benzenacetic acid (ibufenac), α-methy-4-(2-methylpropyl)benzenacetic acid (ibuprofen) and 1-(4-chlorobenzoyl)-5-methoxy-1H-indole-3-acetic acid (indomethacin).

However these NSAs suffer the disadvantage that when administered orally, they tend to cause irritation of the stomach, even leading to bleeding and stomach ulcers.

A further disadvantage of available NSAs is that they generally are highly hydrophilic and consequently are not readily converted into dosage forms which are adapted to partition into the lipid phase. Also available dosage forms are not readily adapted for transcutaneous administration nor for formulation into convenient sustained release forms.

In an attempt to avoid these disadvantages a class of NSAs has been developed, which contain a basic nitrogen atom or atoms, which may be present for example as primary, secondary or tertiary amino groups, or other nitrogen-containing groups, such as amido groups. Examples include 2-((2,6-dichloro-phenyl)amino)benzene-acetic acid (diclofenac) and (4-hydroxy-2-methyl-N-2-pyrydinyl-2H-1,2-benzothiazine-3-carboxamide 1,1-dioxide (piroxicam).

SUMMARY OF THE INVENTION

We have now developed a novel class of NSA derivatives which avoid these disadvantages.

Thus according to the present invention there are provided salts of phosphatidic acids and basic NSAs. Generally, the basic NSAs used to form salts according to the invention are NSAs containing one or more basic nitrogen atom, for example primary, secondary or tertiary amino groups.

The salts of the invention may be represented by the formula $$[NSA]_x[PA]_y \qquad (III)$$

wherein

NSA represents a cation derived from said non-steroidal anti-inflammatory analgesic and/or antipyretic substance, PA represents a phosphatidic acid or a mixture of different phosphatidic acids, and x:y is from 2:1 to 1:2.

In the novel salts of the invention, the non-steroidal anti-inflammatory, analgesic and/or antipyretic substance is preferably diclofenac (2-((2,6-dichlorophenyl)amino)benzene-acetic acid) or piroxicam (4-hydroxy-2-methyl-N-2-pyrydinyl-2H-1,2-benzothiazine-3-carboxamide 1,1-dioxide).

The term "phosphatidic acid" as used herein, can represent a compound having the formula.

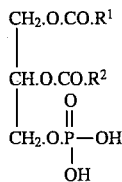

wherein $R_1$ and $R_2$, which may be the same or different each represents a $C_{10-24}$ alkyl group, a $C_{10-24}$ alkenyl group, or a $C_{10-24}$ alkadienyl group. Said groups may be represented by the formulae $C_nH_{2n+1}$, $C_nH_{2n-1}$ or $C_nH_{2n-3}$ Preferably, n is from 15 to 24, most preferably 15 or 17.

In mope specific terms, the present invention relates to new salts of basic NSAs with phosphatidic acids that exhibit increased bioavailability when administered by mouth, rectally, transcutaneously or transepicutaneously. For reasons explained below, the trancutaneous and transepidermal routes are the administration routes of choice for the new substances according to the invention.

The new salts of the invention are highly lipophilic and have a high level of bioavailability when administered by mouth or transcutaneously or transepidermally. The new salts are of particular value, when incorporated in adhesive plasters or suitable gels or appropriate pharmaceutical forms, for the treatment of localised inflammatory processes where an appropriate concentration of the drug can rapidly reduce the disease concerned.

The products are suitable for use in the fields of dermatology, orthopaedics and internal medicine; they are also of wide application in the systemic treatment of painful and febrile conditions of inflammatory origin.

According to a further aspect of the invention there are provided pharmaceutical compositions comprising a salt according to the invention, preferably one of the preferred salts referred to above, and a pharmaceutically acceptable excipient.

The salts according to the invention are especially well adapted for formulation into sustained release pharmaceutical dosage forms capable of releasing their pharmacologically active substance (i.e. the non-steroidal anti-inflammatory, analgesic and/or antipyretic substance) over a period of time and in particular to release the pharmaceutically active substance trans-cutaneously.

For this purpose, the sustained release forms are preferably in the form of a cutaneous patch, plaster or bandage.

The salts of the invention may be prepared by a process comprising salification of (a) basic NSAs and (b) one or more phosphatidic acids, each of said reactants (a) and (b) being in free form or in the form of a salt-forming derivative.

The salification is preferably carried out in a solution for both reactants.

The solvent is preferably selected from halogenated hydrocarbons, ketones, ethers and mixtures thereof.

Suitable phosphatidic acids for use as salifying agents are natural or synthetic phosphatidic acids. In general these possess acyl chains (which may be the same or different and may be saturated or unsaturated) linked via an ester bond to the oxygen atoms of glycerol. Included are natural phosphatidic acids comprising compounds having different fatty acids present in the ratio corresponding to the natural ratio in the compounds from the plant or animal tissue from which they originate.

The salification is normally carried out in aprotic solvents, generally starting from NSAs in the form of the free base or salified with weak acids and from free phosphatidic acid(s). Alternatively, the salification may be carried out using a trans-salification procedure (or double decomposition reaction) in which a salt of an NSA with an anion $X^-$ is reacted with a salt of a phosphatidic acid with a cation $Y^+$, wherein the salt $Y^+.X^-$ is essentially insoluble in reaction medium. An example is the reaction of a hydrochlorate of an NSA with a sodium or potassium salt of phosphatidic acid(s).

The salts of the NSAs thus obtained are highly soluble in non-protic solvents, from which they can be isolated by concentration and if necessary evaporation to dryness or by insolubilisation in non-solvents such as hexane or petroleum ether.

The salts may normally be obtained by reacting the reagents in molar proportions (1M:1M). Salification is generally complete when complete solubility of the reagents in the chosen solvent is achieved.

When treated with water, the novel salts of the invention can adopt a micellar form and distribute themselves quantitatively in non-miscible lipophilic organic solvents. The salts of the invention are believed to acquire their lipophilic character from the ability of the acyl chains to wrap themselves around the most polar central nucleus i.e. the region of the molecule constituted by the basic NSAs, with the result that they can form a liposomal microdispersion in aqueous media.

It has surprisingly been found that when the novel salts of the invention are administered in the form of gelled aqueous microdispersions (lipogels), or incorporated in controlled release plasters applied to various parts of the body, they have considerable therapeutic advantages over the traditional dosage forms of NSAs. It has been shown that in these dosage forms the new salts according to the invention have a different level of bioavailability, with an attendant positive effects on their activity.

It has also been found (and this constitutes one of the most important aspects of the invention) that when the lipophilic salts of the NSAs are applied topically, e.g. in controlled-release formulations, especially ones in liposomal or pseudoliposomal form, they can interact rapidly with the cell structures and diffuse rapidly through the tissues where they can easily gain access to the desired site of action.

One of the aims of the invention concerns in particular the topical application of these new substances for the treatment of inflammatory changes attributable to rheumatoid arthritis or degenerative joint diseases of similar origin.

These new salts can be applied to the above sites in dosages of between 10 and 2000 mg given as one or more doses per day.

It is clear that if consistent results are to be obtained in chronic inflammatory diseases there must be a constant supply of the drug to the target organ in quantities sufficient to produce the required effect. This may be achieved using salts according to the invention.

Controlled-release transcutaneous pharmaceutical forms have proved suitable for the administration of the new salts according to the invention since they enable the drug to be directed to the target organ with minimal transfer to sites where the drug is not required or is poorly tolerated (e.g. the stomach).

Controlled-release plasters have proved to be particularly effective for this purpose.

Liposomal forms of the same salt applied in the form of lipogels, with or without the presence of conventional phospholipids, have also proved effective. The plaster form has also proved extremely practical for long-term use. The salts according to the invention can also be incorporated and administered in other conventional forms such as oily solutions, gels, ointments, creams, lotions, tablets, capsules, suppositories, and occlusive dressings. It is one particular advantage of the salts of the invention that they salts can be dissolved in unsaturated vegetable oils with a vasokinetic action such as the esters of ximeninic acid or of eicosapentenoic acids, etc. These oils in which the salts according to the present invention are freely soluble, can constitute an appropriate vehicle that is capable of increasing the permeation of the tissues by the products. Solutions of the new anti-inflammatory salts in this oily matrix can be used in the treatment of psoriasis and many forms of dermatitis in which the inflammatory process is associated with changes in the microcirculation.

The salts according to the invention can be applied in the form of aqueous microdispersions or lipogels or in conventional gels and emulsions to large areas of the body such as the upper and lower limbs to treat deep inflammation.

The new salts according to the invention produce better results than the NSAs themselves under these conditions because they are better distributed in the surface tissue and remain present at the site of action for longer periods of time.

DETAILED DESCRIPTION

The following pharmacological data illustrates the use of the novel salts of the invention and their advantages over available NSAs.

In a first series of experiments the reduction of croton oil-induced oedema in the mouse was studied, using the method described by Bri P. et al., Agents and Actions 17, 347 (1985).

The results appear in the following Table I:

TABLE I

Reduction in croton oil-induced oedema in the mouse after the administration of salts of dipalmitoylphosphatidic acid with diclofenac

| Substances | Dose | % reduction in oedema |
| --- | --- | --- |
| Controls | — | — |
| Phosphatic acid (PhA) | 0.3 uM | 12.5 |
|  | 0.5 uM | 32.6 |
| Diclofenac (DicF) | 0.1 uM | — |
|  | 0.3 uM | 18.2 |
|  | 1 uM | 27.2* |
| DicF-PhA salt | 0.3 uM | 49.2* |
|  | 0.5 uM | 65.1* |
|  | 1 uM | 84.2* |

*$p < 0.05$ Student t test

In a second series of experiments the effects in rheumatoid arthritis induced in the rat by an injection of bacterial toxin (Freund adjuvant) into the paw. In this test the rat's paw was treated topically by immersing it in an aqueous microdispersion of the salt, so as to simulate topical treatment in man.

The substances were applied topically in the form of microdispersions in water; the arthritis was induced and the measurements taken by the method described by Winter and Nuss, 1966.

TABLE II

Antiarthritic activity of the salt of dipalmitoyl-phosphatidic acid with piroxicam in the rat

| Substances | No. of rats | Dose | Reduction in volume of paw |
|---|---|---|---|
| Piroxicam (PiC) | 12 | 20 | 14% |
|  | 12 | 40 | 22%* |
|  | 11 | 60 | 28%* |
| Phosphatidic Acid (PhA) | 12 | 100 | — |
| PiC-PhA salt | 12 | 60 | 35%* |
|  | 12 | 120 | 62%* |
|  | 10 | 180 | 73%* |

*$p < 0.05$ Student's t test

Example I

Preparation of the salt of hydrogenated soya phosphatidic acid with 2-((2,6-dichlorophenyl)amino-benzeneacetic acid.

2.97 g 2-((2,6-dichlorophenyl)amino)benzeneacetic acid are dissolved in 15 ml methylene chloride with stirring and 7 g hydrogenated soya phosphatidic acid (natural ratio of fatty acids) with a mean molecular weight, determined by acid-base titration, of 698 are added.

When the reagents have dissolved completely, the solution in methylene chloride is evaporated to dryness under vacuum at a temperature not exceeding 40° C. until the solvent has been completely eliminated. The residue is dispersed in n-hexane at 5° C. and filtered.

This yields 9.5 g or an amorphous white solid with an unknown melting point and a $[\alpha]_D$ (conc 0.5% in $CHCl_3$= +6.82) $_{31}$P-NMR 0.45, 0.03 ppm.

Example II

Preparation of the salt of hydrogenated soya phosphatidic acid with 4-hydroxy 2-methyl-N-2-pyrydinyl-2H-1,2-benzothiazine-3-carboxamide 1,1-dioxide 3.3 g 4-hydroxy-2-methyl-N-2-pyrydinyl-2H-1,2-benzothiazine-3-carboxamide 1,1-dioxide are dissolved in 15 ml methylene chloride with stirring and 7 g hydrogenated soya phosphatidic acid (natural ratio of fatty acids) with a mean molecular weight, determined by acid-base titration, of 698 are added.

When the reagents have dissolved completely, the solution in methylene chloride is evaporated to dryness under vacuum at a temperature not exceeding 40° C. until the solvent has been completely eliminated. The residue is dispersed in n-hexane at 5° C. and filtered.

This yields 10 g of an amorphous white solid with an unknown melting point and a $[\alpha]_D$ (conc 0.5% in $CHCl_3$= +5.77) $_{31}$P-NMR 0.62, 0.25 ppm.

Example III

Oily lotion containing the phosphatidate of 4-hydroxy 2-methyl-N-2-pyrydinyl-2H-1,2-benzothiazine-3-carboxamide 1,1-dioxide 0.5 g of the phosphatidate of 4-hydroxy-2-methyl-N-2-pyridinyl-2H-1,2-benzothiazine-3-carboxamide 1,1-dioxide are dissolved in 50 ml ethylximeninate; this pharmaceutical form is applied directly to the skin and is useful in the treatment of psoriasis and joint diseases.

Example IV

Lipogel containing the phosphatidate of 4-hydroxy-2-methyl-N-2-pyrydinyl-2H-1,2-benzothiazine-3-carboxamide 1,1-dioxide To prepare 100 g lipogel, 1 g 4-hydroxy-2-methyl-N-2-pyridinyl-2H-1,2-benzothiazine-3-carboxamide 1,1-dioxide phosphatidate is mixed with 15 g pure soya phosphatidylcholine and the whole is dispersed in 83 g water; when microdispersion has taken place, 0.5 g carboxymethyl-cellulose is added as a thickener. The lipogel is useful in the treatment of atopic dermatitis and as a coadjuvant in rheumatoid arthritis.

We claim:

1. A salt of a non-steroidal anti-inflammatory, analgesic and/or antipyretic substance (NSA) and a phosphatidic acid, said salt having the formula $$[NSA]_x[PA]_y$$

wherein

NSA represents a cation derived from said non-steroidal, anti-inflammatory, analgesic and/or antipyretic substance; PA represents a phosphatidic acid or a mixture of different phosphatidic acids, each of said phosphatidic acid or phosphatidic acids having the formula

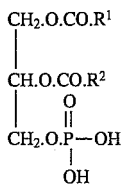

wherein $R_1$ and $R_2$, which may be the same or different, each represents a $C_n$ alkyl group, a $C_n$ alkenyl group, or a $C_n$ alkadienyl group wherein n is an integer from 10 to 24; and x and y are in a stoichiometric ratio of 1:1.

2. A pharmaceutical composition comprising a salt according to claim 1 and a pharmaceutically acceptable excipient.

3. A sustained release pharmaceutical dosage form capable of releasing an NSA over a period of time, comprising as a pharmaceutically active substance a salt according to claim 1.

4. A method for the treatment of inflammatory conditions of the skin or joints in a patient which comprises administering to the patient an effective amount of a salt according to claim 1.

5. A salt according to claim 1 wherein the NSA is 2-((2,6-dichloro-phenyl)amino)-benzene-acetic acid (diclofenac) or (4-hydroxy-2-methyl-N-2-pyrydinyl-2H-1, 2benzothiazine-3-carboxamide 1,1-dioxide (piroxicam).

6. A salt according to claim 1 wherein n is from 15 to 24.

7. A salt according to claim 6 wherein n is 15 or 17.

8. A salt according to claim 1 wherein NSA is a cation derived from 2-((2,6-dichloro-phenyl)amino)benzene-acetic acid (diclofenac) or (4-hydroxy-2-methyl-N-2-pyrydinyl-2H-1,2-benzothiazine-3-carboxamide 1,1-dioxide (piroxicam).

9. A pharmaceutical composition according to claim 2 wherein said excipient comprises an unsaturated vegetable oil.

10. A sustained release pharmaceutical dosage form as claimed in claim 3, adapted to release the pharmaceutically active substance trans-cutaneously.

11. A sustained release pharmaceutical dosage form according to claim 10 in the form of a cutaneous patch, plaster or bandage.

* * * * *